United States Patent [19]
Berger

[11] Patent Number: 5,545,136
[45] Date of Patent: Aug. 13, 1996

[54] GROOVED CATHETER DIRECTOR APPARATUS

[76] Inventor: J. Lee Berger, 895 Mohawk Rd., Franklin Lakes, N.J. 07417

[21] Appl. No.: 369,869

[22] Filed: Jan. 5, 1995

Related U.S. Application Data

[63] Continuation of Ser. No. 120,518, Sep. 14, 1993, abandoned.

[51] Int. Cl.$^6$ .................................................. A61M 29/00
[52] U.S. Cl. ............................. 604/96; 606/192; 128/898
[58] Field of Search .............................. 604/93, 96, 104, 604/158, 159, 160, 280; 606/192; 128/898

[56] References Cited

U.S. PATENT DOCUMENTS

| | | | |
|---|---|---|---|
| 1,109,626 | 9/1914 | Davis | 604/280 |
| 2,164,926 | 7/1939 | Kleine . | |
| 3,472,232 | 10/1969 | Earl | 604/160 |
| 3,537,452 | 11/1970 | Wilks . | |
| 3,559,643 | 2/1971 | Pannier et al. . | |
| 3,592,193 | 7/1971 | Higgins . | |
| 3,742,958 | 7/1973 | Rundles | 604/160 |
| 3,827,434 | 8/1974 | Thompson et al. | 604/160 |
| 3,833,004 | 9/1974 | Vasquez et al. . | |
| 4,250,881 | 2/1981 | Smith | 128/214.4 |
| 4,311,140 | 1/1982 | Bridgman . | |
| 4,552,554 | 11/1985 | Gould et al. | 604/104 |
| 4,629,450 | 12/1986 | Suzuki et al. | 604/104 |
| 4,645,491 | 2/1987 | Evans . | |
| 4,655,214 | 4/1987 | Linder . | |
| 4,684,363 | 8/1987 | Ari et al. . | |
| 4,798,586 | 1/1989 | Stevens . | |
| 4,800,901 | 1/1989 | Rosenberg . | |
| 4,842,585 | 6/1989 | Witt | 604/158 |
| 4,888,000 | 12/1989 | McQuilkin et al. | 604/160 |
| 4,921,484 | 5/1990 | Hillstead . | |
| 4,932,958 | 6/1990 | Reddy et al. . | |
| 4,962,770 | 10/1990 | Agee et al. . | |
| 4,963,147 | 10/1990 | Agee et al. . | |
| 5,011,478 | 4/1991 | Cope . | |
| 5,021,043 | 6/1991 | Becker et al. . | |
| 5,029,573 | 7/1991 | Chow . | |
| 5,044,369 | 9/1991 | Sahota | 604/96 |
| 5,084,060 | 1/1992 | Freund et al. . | |
| 5,089,000 | 2/1992 | Agee et al. . | |
| 5,143,093 | 9/1992 | Sahota . | |
| 5,163,949 | 11/1992 | Bonutti . | |
| 5,179,963 | 1/1993 | Berger . | |
| 5,183,464 | 2/1993 | Dubrul et al. . | |
| 5,188,630 | 2/1993 | Christoudias . | |
| 5,195,989 | 3/1993 | Euteneuer . | |
| 5,197,971 | 3/1993 | Bonutti . | |
| 5,209,727 | 5/1993 | Radisch, Jr. et al. . | |
| 5,273,024 | 12/1993 | Menon et al. . | |

Primary Examiner—Randall L. Green
Assistant Examiner—Perry E. Van Over

[57] ABSTRACT

A surgical instrument used in conjunction with treatment of carpal tunnel syndrome includes a tubular member having a lumen extending therethrough and terminating at a blunt distal end. An opening extends through the peripheral wall of the tubular member and in communication with the lumen. A catheter possessing an expandable member is positioned within the lumen of the tubular member. The expandable member expands through the opening in the peripheral wall of the tubular member to engage and stretch the transverse carpal ligament so as to relieve pressure off the median nerve within the carpal tunnel.

27 Claims, 2 Drawing Sheets

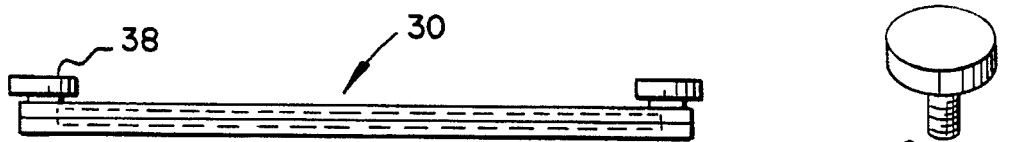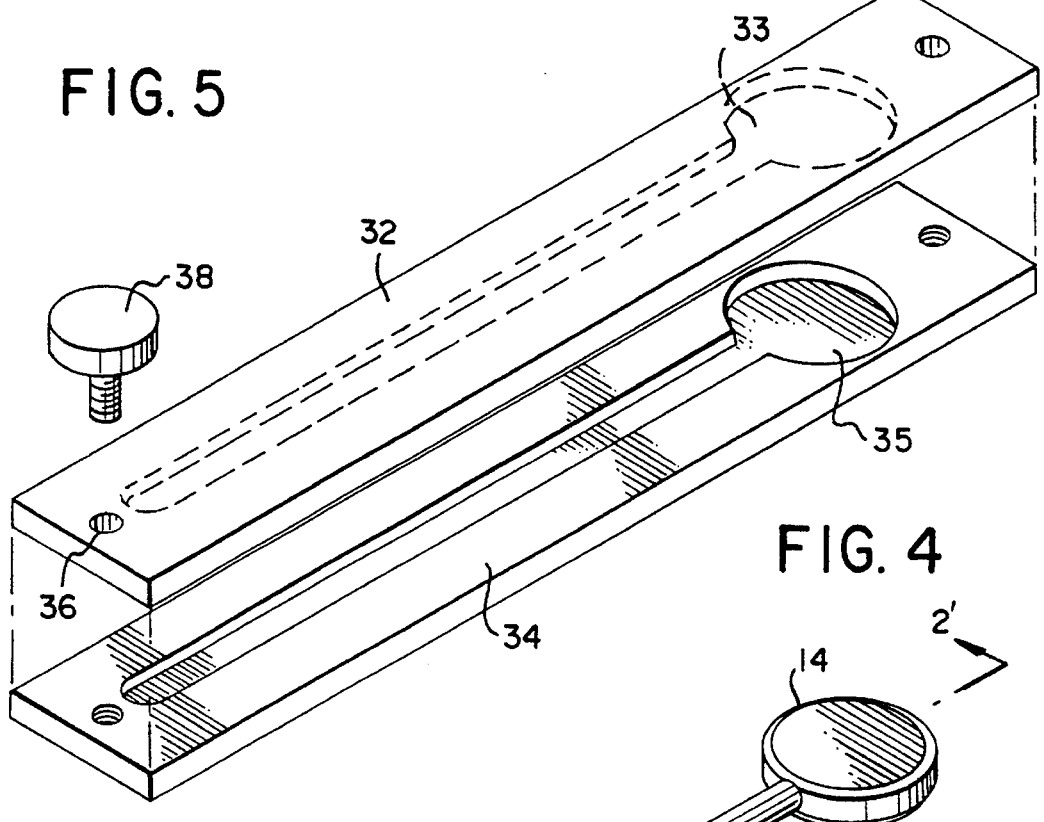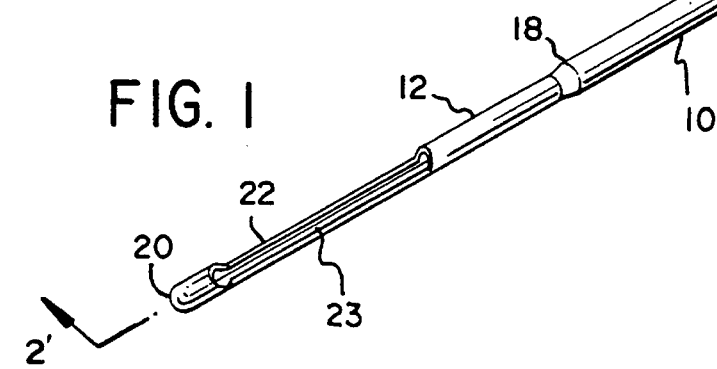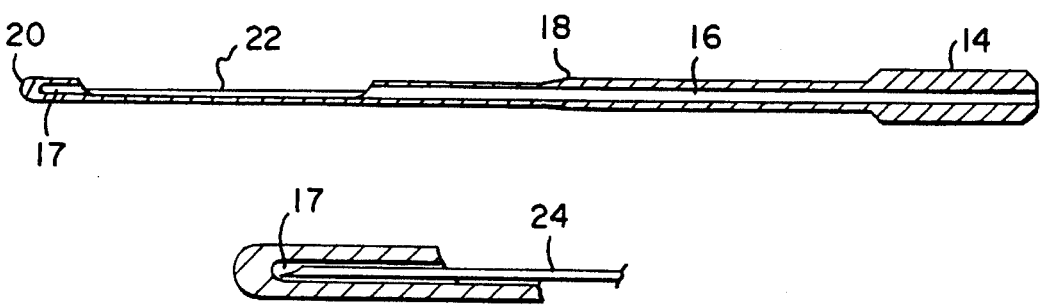

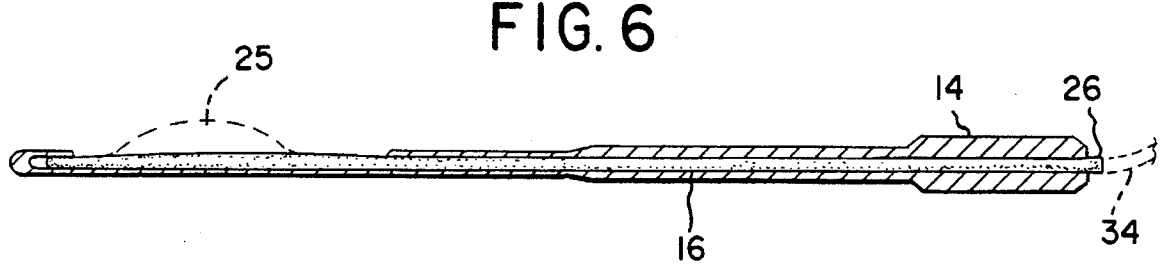
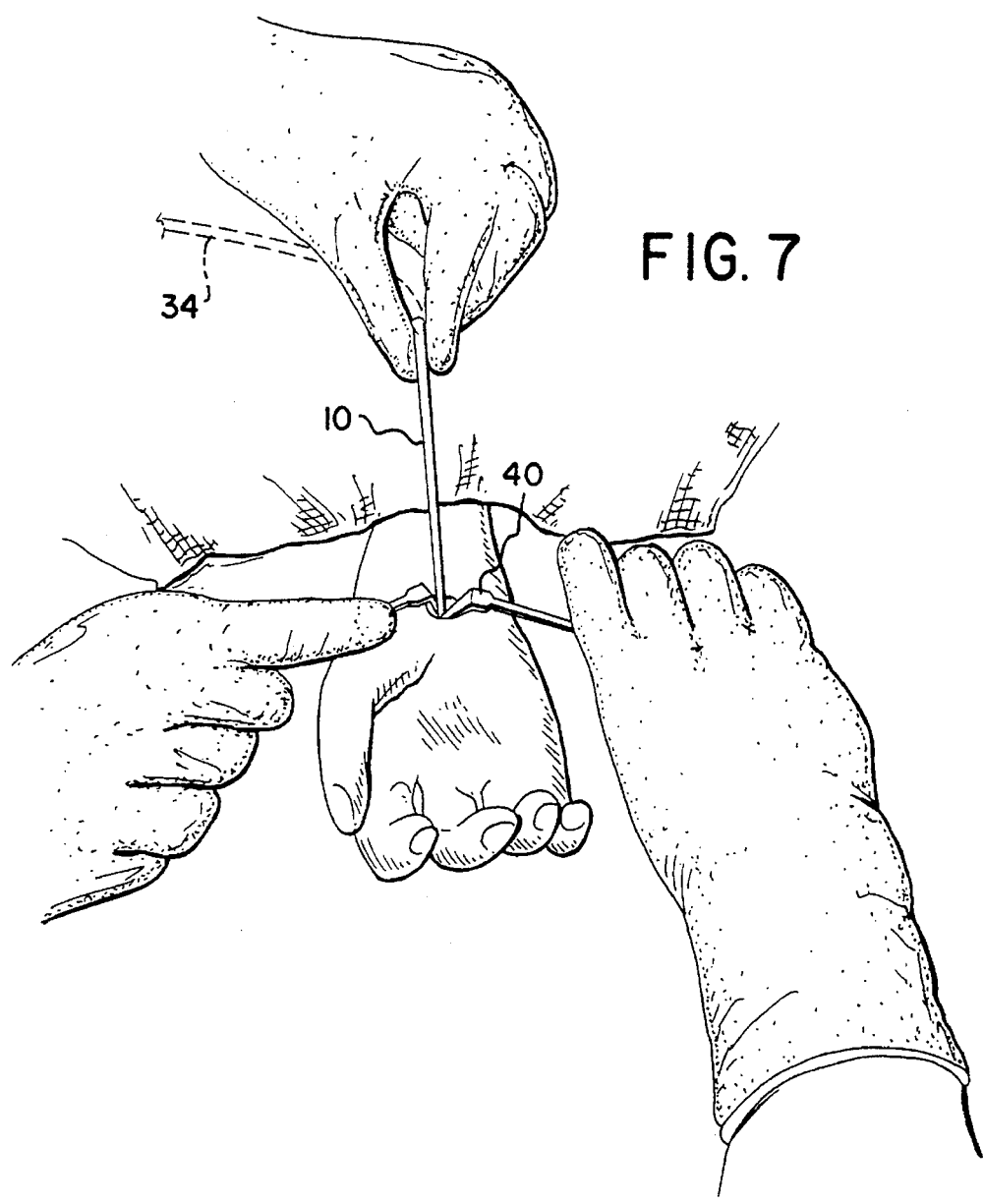

GROOVED CATHETER DIRECTOR APPARATUS

This is a continuation, of application Ser. No. 08/120,518 filed on Sep. 14, 1993.

BACKGROUND OF THE INVENTION

1. Field of the Invention

The present invention relates generally to a cannula used as an aid for insertion of catheters and other instruments into the body of a patient and more particularly to a grooved balloon catheter director apparatus used in surgical procedures such as Carpal Tunnel Syndrome.

2. Brief Description of the Background

It is a frequent practice when introducing balloon catheters and other catheters or instruments into the body to first introduce a cannula or sheath to aid in the introduction of the catheter or other instruments. The present invention is directed to the use of a grooved catheter director apparatus used in surgical procedures such as Carpal Tunnel Syndrome which increases the spatial diameter of the carpal tunnel enclosing the nerve.

Historically, carpal tunnel syndrome has been treated nonsurgically by splinting of the affected hand and wrist, oral anti-inflammatory medication, and local steroid injection. If nonsurgical methods are unsuccessful, surgical intervention is required.

Open surgical decompression of the carpal tunnel by division of the transverse carpal ligament was first described in 1930 by Learmonth. Open procedures generally entail a curved longitudinal incision parallel to the thenar crease. Taleisnik has described an incision along the ulnar border of the ring finger axis (Taleisnik, J.: The palmar cutaneous branch of the median nerve and the approach to the carpal tunnel: An anatomical study; J. Bone Joint Surg, 55A: 1212, 1973). This incision may be extended proximally to the wrist flexor crease. Angling the incision towards the ulnar aspect of the wrist helps to avoid cutting the palmar sensory cutaneous branch of the median nerve. This nerve is located in the interval between the palmaris longus and the flexor carpi radialis tendons. After division of the skin and subcutaneous tissue, the transverse carpal ligament is identified and divided along its ulnar border to avoid and to prevent injury to the median nerve or its recurrent branch. It is to this application that the present grooved director device has been developed.

Various patents disclose devices for inserting or placing catheters within chosen parts of the human body. U.S. Pat. No. 4,655,214 discloses a soft inflatable sheath having a closed rounded distal tip that is inserted through a catheter and inflated adjacent the distal tip of the catheter prior to intubation. The proximal end of the sheath is sealed to maintain it in expanded inflatable condition when the catheter is being intubated. Following intubation the cylindrical sheath is deflated and withdrawn. U.S. Pat. No. 4,645,491 discloses a catheter placement apparatus used in inserting a catheter to a preferred depth. The device comprises a surgical needle provided with a thin-walled transparent polytetrafluoroethylene tube which is heat shrunk over the stem portion of the needle to form a longitudinal window allowing a catheter inserted in the needle to be viewed. The catheter has a colored patch of the same length as the window and a series of spaced circular bands of differing colors allowing the position of the catheter to be accurately located by lining the colored patch with the window and advancing the catheter until at least one band appears in the window. The color and distance of the band nearest to the surface of the patient's skin are used to determine the position of the catheter. The needle is withdrawn by sliding it along and off the catheter. U.S. Pat. No. 2,164,926 discloses a catheter stylet with an eye or aperture positioned on an opposite lateral wall behind the tip. U.S. Pat. No. 3,537,452 discloses a needle guard and beveled cutter for use with intravenous catheterization units. The device has a tubular body with a flat base and a longitudinally slotted top. The diameter of the tube is greater than the diameter of the needle contained therein. U.S. Pat. No. 3,592,193 discloses a removable needle guide to be used with a flexible catheter tube in withdrawing or introducing fluids relative to a body. The hollow tubular needle guide has a sharpened needle portion provided at its proximal end for puncturing the skin, tissues and veins of the body where the needle is inserted. At its distal end, winged handles are associated therewith which provide controlled insertion and removal from the body with subsequent attachment from a flexible catheter tube. U.S. Pat. No. 5,011,478 discloses an introducer set including a sheath and dilator formed with a smooth external shape. The distal end of the sheath is embedded in the dilator and formed in angle oblique to the longitudinal access of the introducer set. U.S. Pat. No. 3,559,643 discloses a catheter placement unit for insertion of a catheter into a body lumen through an incised opening in the lumen wall. The unit includes a longitudinally slit sheath having a catheter therein and an advancer connected to one end of the catheter, initially in axial alignment with the sheath to close the end of the sheath.

None of the aforenoted prior art has provided a solution to problems found in carpal tunnel surgery.

SUMMARY OF THE INVENTION

The present invention is directed to a protective carpal tunnel grooved director catheter device which is housed prior to use in a protective case. The grooved director device is easily placed underneath the transverse carpal ligament and inserted distally to the most distal margin of the transverse carpal ligament. The protective grooved director device serves to direct a balloon catheter in the carpal tunnel and protects the medial nerve and underlying structures. The balloon catheter which is mounted in the director device is utilized to dilate and expand the transverse carpal ligament, through serial applications of fluid pressure expanding the balloon while it is moved along the carpal tunnel, thereby increasing the diameter of the carpal tunnel, thus relieving compression of the median nerve and alleviating the symptoms of carpal tunnel syndrome.

Thus, percutaneous dilatation of the transverse carpal ligament increases the spatial diameter of the carpal tunnel and relieves pressure on the median nerve in the hand and wrist.

The objects and advantages of the present invention are that it protects the median nerve, blood vessels and flexor tendons upon insertion and use of the balloon catheter.

The position of the grooved director and balloon catheter can be monitored throughout the procedure by image intensifier or x-ray control.

It is an object of the invention to provide a catheter guide director which can be positioned in a human being allowing use of a balloon catheter without applying undue force to the catheter.

It is a further object to provide a device which can be manufactured at a reduced cost and which is disposable after use.

It is a further object to provide a combined balloon catheter and guide device which can be easily manufactured and which is disposable after use.

Additional objects and advantages of the invention are that the grooved catheter director device allows the carpal tunnel procedure to be performed with or without endoscopic assistance. The procedure performed with the grooved catheter is simple and safe and the incision is minimal with a very cosmetic result.

In the accompanying drawings, there is shown an illustrative embodiment of the invention from which these and other of objectives, novel features and advantages will be readily apparent.

BRIEF DESCRIPTION OF THE DRAWINGS

FIG. 1 is a perspective view of the protective grooved director device of the present invention;

FIG. 2 is a cross sectional view of the grooved director device taken along line 2'—2' of FIG. 1;

FIG. 3 is an enlarged cross sectional view of the tip of the grooved director device shown in FIG. 2 with a catheter mounted therein;

FIG. 4 is an exploded perspective view partially in phantom of the casing for the grooved director device of FIG. 1;

FIG. 5 is an assembled side elevational view of the grooved director casing shown in FIG. 4;

FIG. 6 is a cross sectional view of an alternate embodiment of the grooved director device with integral balloon catheter taken along line 2'—2' of FIG. 1; and FIG. 7 is a schematic view showing the grooved director device in place in a patient with the balloon inflated during the serial inflation and deflation of the balloon catheter.

DETAILED DESCRIPTION OF THE INVENTION

A preferred embodiment and best mode of the invention is shown in FIGS. 1–3. The protective grooved director device 10 is constructed of a single piece of stainless steel or plastic tube 12 and a rounded disc shaped handle 14 which can be screwed or mounted onto the tube with adhesive or sonic welding. If desired both the handle and tube can be formed from a single piece of material such as stainless steel or rigid medically approved plastic material as for example polyethylene or polypropylene. A throughgoing lumen 16 extends through the handle and terminates near the distal end 20 of the tube 12 to form a blind bore 17. The tube 12 is stepped at 18 to provide a thinner diameter tube while providing strength near the handle and has a blunt distal end 20. The tube is cutout at 22 to expose the lumen 16 and form an open groove 23 allowing a balloon catheter 24 which has been placed in the lumen of the grooved director to be expanded.

In an alternate embodiment shown in FIG. 6 a balloon catheter 24 has been mounted and secured in lumen 16 so that the grooved director and the balloon catheter form a single assembly. The proximal end 26 of the balloon catheter extends past the disc shaped handle 14 to receive a connector fitting of the conventional "Luer" female type or a valve fitting and the distal end is seated in blind bore 17. The balloon catheter 24 can be constructed of latex rubber, polyvinyl chloride or suitable medically approved material. The seating of the catheter allows the balloon portion 25 to be positioned in cutout portion 22 so that the same can be serially inflated and deflated as it is moved along the carpal tunnel.

The grooved director device 10 as seen in FIGS. 4 and 5 is housed in a case 30 constructed of two planar sections 32 and 34, each of which has a mirror image cutout 33 and 35 respectively of the form of the grooved director device. Both of the sections are provided with threaded holes 36 at each end which receive threaded thumb screws 38 to hold the sections and enclosed groove director device in a secure and locked position thus preventing breakage, bending and fouling of the device.

In operation and use of the grooved director device 10 an incision is cut through the skin and subcutaneous tissue by sharp dissection. A self retaining retractor 40 is placed in the wound. The most proximal portion of the transverse carpal ligament is identified. With care to protect the underlying median nerve, the protective carpal tunnel grooved director device 10 is placed underneath the transverse carpal ligament and inserted distally to the most distal margin of the transverse carpal ligament. The balloon catheter 24 is attached to the pressure monitor and syringe (not shown). Initial pressure reading is taken of the carpal tunnel. Sterile saline solution is then injected from the syringe into the balloon catheter 24 via tube 34 and the distal dilation bulb or balloon 25 of the catheter is expanded in the most distal portion of the carpal canal. The position of the radio opaque catheter and balloon is confirmed by either image intensification or radiographs. The carpal tunnel-plasty is performed by serially inflating and deflating the balloon catheter 24 intermittently along the course of the carpal tunnel from distal to proximal dilating and permanently stretching the transverse carpal ligament. When the balloon catheter 24 is inflated, the protective grooved director has been designed to prevent compression on the median nerve and underlying structures. The median nerve remains protected avoiding cicatrix formation in the carpal tunnel and perineural fibrosis. The normal relationship of the carpal tunnel and its contents are thereby maintained. The position of the balloon catheter can be monitored with image or x-ray control. The protective grooved director device 10 serves to direct the balloon catheter 24 in the carpal tunnel and protect the medial nerve and underlying structures. At the conclusion of the dilatation of the transverse carpal ligament, the balloon 25 is deflated and the catheter 24 and protective groove director device 10 are removed. The subcutaneous layer is closed with a suture and the skin is reapproximated.

When the grooved director device is used, the patient has less postoperative pain with a quick recovery time and earlier return to activities of daily living than can be obtained with open or endoscopic carpal tunnel release. A more complete description of the surgical operation is set forth in U.S. Pat. No. 5,179,963 entitled Percutaneous Carpal Tunnel Plasty Method issued Jan. 19, 1993 which patent is incorporated herein by reference.

In the foregoing description, the invention has been described with reference to a particular preferred embodiment, although it is to be understood that specific details shown are merely illustrative, and the invention may be carried out in other ways without departing from the true spirit and scope of the following claims.

What is claimed:

1. A director device to assist in insertion of a balloon catheter, comprising an elongated substantially rigid tubular member dimensioned to be inserted through tissue and defining a longitudinal axis, said tubular member having a proximal end portion and a distal end portion with a distalmost closed tip, said tubular member defining a lumen extending therethrough dimensioned to accommodate a balloon catheter inserted therein, said lumen terminating at said distalmost closed tip, said tubular member including a single opening in an outer wall portion thereof in communication with said lumen and being disposed intermediate said proximal and distal end portions of said tubular member such that a distalmost portion of said lumen is disposed beyond said opening, said single opening dimensioned to permit expansion of a balloon of the balloon catheter therethrough upon inflation of the balloon to permit the expanded balloon to engage and dilate tissue, wherein surface edges of said outer wall portion defining and surrounding said single opening are substantially blunt to avoid penetration of the balloon upon expansion thereof through said single opening and, wherein said distalmost portion of said lumen is dimensioned to receive and accommodate a distal end of a balloon catheter and further wherein distal axial movement of the catheter relative to said tubular member is limited by engagement of the catheter distal end with said distalmost closed tip of said tubular member.

2. The director device as claimed in claim 1, wherein a handle is connected to said proximal end portion of said tubular member, said handle having a thoroughgoing lumen in general alignment and in communication with said lumen of said tubular member.

3. The device as claimed in claim 2 wherein said tubular member and said handle are integrally formed from plastic.

4. The device as claimed in claim 2 wherein said tubular member and said handle are integrally formed from stainless steel.

5. The device as claimed in claim 2 wherein said distalmost closed tip of said tubular member has an outer surface which is rounded.

6. The device as claimed in claim 2 wherein said handle is disc shaped.

7. The device as claimed in claim 2 including a case housing said device.

8. The device as claimed in claim 1 wherein said proximal end portion of said tubular member defines a cross-sectional dimension greater than the cross-sectional dimension defined by said distal end portion of said tubular member.

9. The device as claimed in claim 1 wherein said tubular member defines said single opening which extends around the periphery of said tubular member for at least greater than one-half the length of the periphery.

10. A surgical apparatus to assist in dilating tissue which comprises:

a substantially rigid tubular member dimensioned to be inserted through tissue and having proximal and distal end portions, said tubular member defining a lumen extending therethrough and terminating at said distal end portion thereof, an outer wall portion of said tubular member having a single opening in communication with said lumen and being defined by surface edges of said outer wall portion surrounding said single opening, said single opening being disposed intermediate said proximal and distal end portions of said tubular member such that a distalmost portion of said lumen is disposed beyond said single opening, said surface edges being substantially blunt; and a catheter at least partially supported within said lumen of said tubular member, said catheter including an elongated member defining a passageway for passage of fluids and an expandable member in communication with said passageway, said expandable member positioned adjacent said single opening in said outer wall portion and expandable to a predetermined configuration in response to inflation thereof, wherein said expandable member when in said predetermined configuration extends outwardly through said single opening in said outer wall of said tubular member to engage and dilate adjacent tissue.

11. The apparatus as claimed in claim 10, wherein said distal end portion of said tubular member defines a distalmost blunt closed tip, said blunt closed tip engaging said distal end of said elongated member of catheter upon positioning of said catheter within said lumen to prevent further axial movement of said catheter.

12. The apparatus as claimed in claim 10, wherein said catheter is connected to said tubular member and wherein said expandable member is positioned adjacent said opening.

13. The apparatus as claimed in claim 12, wherein said expandable member is secured to said tubular member at a position adjacent said opening.

14. The apparatus as claimed in claim 10, wherein said proximal end portion of said tubular member has a handle attached thereto and dimensioned to facilitate handling of said tubular member.

15. The apparatus as claimed in claim 14, wherein said handle includes a lumen in general alignment with and in communication with said lumen of said tubular member.

16. The apparatus as claimed in claim 14 wherein said catheter has a proximal end which extends proximally of said handle.

17. The apparatus as claimed in claim 16 wherein said proximal end of said balloon catheter includes a connector means mounted thereto.

18. The apparatus as claimed in claim 17 wherein said connector means is a leur lock.

19. The apparatus as claimed in claim 10 wherein said tubular member defines said single opening which extends around the periphery of said tubular member for greater than at least one-half the length of the periphery.

20. A surgical apparatus for dilating tissue, which comprises:

a substantially rigid tubular member dimensioned to be inserted through tissue, said tubular member defining a lumen extending therethrough and terminating at a closed distal tip of said tubular member, an outer wall of said tubular member including a generally longitudinally extending single groove being defined by blunt surface edges of said outer wall surrounding said single groove, said single groove in communication with said lumen and being spaced from said closed distal tip such that a distalmost portion of said lumen is disposed beyond said single groove; and a catheter at least partially disposed within said lumen of said tubular member, said catheter including an elongated member defining a passageway for passage of fluids and a balloon member in communication with said passageway, said balloon member axially secured to said tubular member at a position fixed adjacent said groove of said tubular member such that upon inflation thereof said balloon member expands outwardly through said longitudinal groove to expand adjacent tissue, said elongated member having a distal end portion which is accommodated within said distalmost portion of said lumen.

21. The apparatus as claimed in claim 20 wherein the groove extends around the periphery of said tubular member for a distance which is at least greater than one-half the length of the periphery.

22. A surgical procedure for relieving nerve entrapment syndrome by increasing the spacial diameter of the carpal tunnel enclosing the nerve, comprising the steps of:

providing a guide member dimensioned to be inserted through tissue, said guide member defining a lumen extending therethrough and having an opening in an outer wall portion thereof in communication with said lumen, said lumen terminating at a closed distal tip of said guide member, said opening disposed at a position spaced from said distal tip of said guide member such that a distalmost portion of said lumen is disposed beyond said opening, said opening defining a blunt peripheral edge in said guide member surrounding said opening;

positioning said guide member at least partially beneath the transverse carpal ligament such that the opening is adjacent the transverse carpal ligament;

inserting a catheter within said lumen of said guide member, said catheter including an elongated member defining a passageway for passage of fluids and an expandable member in communication with said passageway;

advancing said catheter within said guide member such that said expandable member is adjacent said opening and a distal end of said elongated member is received within said distalmost portion of said lumen; and inflating said expandable member at least once such that said expandable member extends outwardly through said opening and engages the carpal tunnel ligament to stretch the carpal tunnel ligament.

23. The procedure as claimed in claim 22 wherein the step of positioning includes positioning said guide member such that said opening is adjacent the most distal margin of the transverse carpal ligament.

24. The procedure as claimed in claim 23 wherein the step of inflating includes serially inflating and deflating said expandable member while intermittently moving said guide member along the course of the transverse carpal ligament from distal to proximal.

25. The procedure as claimed in claim 22 wherein the step of inserting said catheter within said lumen of said guide member includes advancing said catheter within said lumen such that said distal end of said elongated member engages said distal tip of said guide member.

26. The procedure as claimed in claim 22 wherein the step of providing includes providing a guide member having an opening in an outer wall portion and wherein said opening extends around the periphery of said guide member for at least greater than one-half the length of the periphery.

27. A surgical apparatus to assist in dilating tissue, which comprises:

an elongated member dimensioned to be inserted through tissue and defining a lumen extending therethrough, an outer wall portion of said tubular member defining an opening in communication with said lumen extending around the periphery of said elongated member for a distance which is at least greater than one-half the length of the periphery; and a catheter at least partially positioned within said lumen of said elongated member, said catheter including an elongated member defining a passageway for passage of fluids and an expandable member in communication with said passageway, said expandable member positioned adjacent said opening in said outer wall portion and expandable to a predetermined configuration in response to inflation thereof with fluids, wherein said expandable member when in said predetermined configuration extends outwardly through said opening to engage and dilate tissue.

* * * * *